(12) United States Patent
Hiyoshi

(10) Patent No.: US 6,460,418 B1
(45) Date of Patent: Oct. 8, 2002

(54) METHOD OF AND APPARATUS FOR MEASURING ELONGATION OF A TEST SPECIMEN

(75) Inventor: Toshio Hiyoshi, Sagamihara (JP)

(73) Assignee: Kishimoto Sangyo Co., Ltd., Osaka-fu (JP)

( * ) Notice: Subject to any disclaimer, the term of this patent is extended or adjusted under 35 U.S.C. 154(b) by 0 days.

(21) Appl. No.: 09/838,120

(22) Filed: Apr. 20, 2001

(51) Int. Cl.[7] .................................................. G01L 3/00
(52) U.S. Cl. ........................................ 73/800; 356/35.5
(58) Field of Search ............................ 73/800; 356/373, 356/394, 330, 32, 35.5

(56) References Cited

U.S. PATENT DOCUMENTS

| | | | | |
|---|---|---|---|---|
| 5,020,904 A | * | 6/1991 | McMahan, Jr. | 356/35.5 |
| 5,568,250 A | * | 10/1996 | Nishiyama et al. | 356/28 |
| 5,568,259 A | * | 10/1996 | Kamegawa | 73/800 |
| 5,747,699 A | * | 5/1998 | Ebi | 356/35.5 |
| 6,006,608 A | * | 12/1999 | Renz et al. | 73/800 |

FOREIGN PATENT DOCUMENTS

| | | |
|---|---|---|
| JP | 59-52963 | 3/1984 |
| JP | 61-27681 | 2/1986 |
| JP | 7-4928 | 1/1995 |

* cited by examiner

*Primary Examiner*—Max Noori
(74) *Attorney, Agent, or Firm*—Armstrong, Westerman & Hattori, LLP

(57) ABSTRACT

Method and apparatus for measuring elongation in a contactless manner capable of obtaining accurate measured value without attaching reference lines and capable of being automated, laser beams are irradiated from two sensor sections each has a laser projector and a CCD camera to prescribed reference line positions at two positions on a test specimen, laser reflection lights are photographed respectively as speckle patterns with a plurality of fringes respectively by the CCD cameras, the fringes at predetermined positions the speckle patterns are recognized on the coordinate of the CCD camera screens as targets correspondingly to the prescribed reference line positions at two positions respectively, and the moving amount on the pixel unit basis on the coordinate of the target fringes that move in accordance with the elongation of the test specimen are detected respectively to determine the elongation information of the test specimen, the fringes of the speckle patterns photographed by the CCD cameras may be image converted into the marks at the predetermined positions of the television camera screens. Stopping or disturbance of image of the speckle patterns of the CCD camera appearing just before the fracture of the test specimen may be sensed to stop the application of the tensile load on the test specimen.

6 Claims, 6 Drawing Sheets

METHOD OF AND APPARATUS FOR MEASURING ELONGATION OF A TEST SPECIMEN

BACKGROUND OF THE INVENTION

1. Field of the Invention

This invention concerns a method of and an apparatus for measuring elongation of a test specimen in a contactless manner without attaching reference lines (or reference points) to a test specimen and, more in particular, it relates to a method of and an apparatus for measuring elongation by utilizing the amount of movement of fringes in speckle patterns that appear in the reflection light of laser beams irradiated to the test specimen.

2. Related Art Statement

As the means for measuring the elongation of a test specimen in a contactless manner, there has been a method of attaching reference lines at two points in the direction of elongation of the test specimen, photographing respective reference lines by two television cameras individually which are recognized by a computer as marks for each of them on a television screens, calculating the moving amount of the marks on the television screens that move along with the elongation of the test specimen, controlling the positions of the two television cameras such that respective marks always situate at predetermined positions displayed on the television screens and measuring the elongation rate based on the difference of the distance in the two television cameras before applying a tensile load and upon rupture of the test specimen.

Further, as the means of measuring the elongation of a test specimen without attaching reference lines in a contactless manner, there have been proposed various methods of and apparatus for measuring elongation in the contactless manner by irradiating a laser beam having an extension for a predetermined length in the direction of exerting a tensile load to the surface of a test specimen and recognizing the reflection light from the region corresponding to reference spots at two positions of the test specimen by electric signals as varying levels of brightness in the speckle pattern, and calculating the elongation of the test specimen based on a correlation function of the electric signals for the speckle pattern by using the output from the image sensor, for example, as disclosed in Japanese Published Unexamined Patent Application Sho 59-52963, Japanese Published Examined Patent Application Sho 61-27681 and Japanese Published Unexamined Patent Application Hei 7-4928.

However, the former method, that is, a method of using the television cameras involves a fetal drawback that reference lines have to be attached to the test specimen. That is, the method of attaching the reference lines includes a method of scratching a test specimen, a method of appending a seal on a test specimen, a method of applying a mark with ink or the like, a method of clipping the test specimen with binders at reference positions. However, the measuring method of appending the reference lines involves problems such as of giving undesired effects on the strength of the test specimen, peeling of the seal, elongation of the reference lines per se making the reference base obscure and, further, causing chemical change to the test specimen by the ink of the reference, which hinders accuracy and efficiency of the test.

On the other hand, the latter method, that is, each of the existent methods of measuring the elongation by utilizing the speckle pattern is adapted for optoelectronically converting reflection light obtained by the irradiation of the laser beam to a portion of a test specimen to be measured by way of an image sensor or the like to obtain electric signals in accordance with the speckle pattern and determining the amount of movement of the speckle pattern based on the correlation function of signals before and after elongation of the test specimen. That is, since the speckle pattern recognized by the image sensor is converted and used as electric signals, it is difficult to attain high measuring accuracy unless precise optical parts and conversion devices are used.

Further, in the existent measurement for elongation by utilizing the speckle pattern is adapted to previously store the speckle pattern in the direction of the elongation of the test specimen before deformation (entire spot pattern) as electric signals and determine the amount of movement of the speckle pattern by continuously deciding the correlation function for the speckle pattern upon deformation relative to the electric signals. Therefore, if the test specimen and the laser beam are laterally displaced relative to each other during measurement, the speckle pattern per se as a reference base becomes inaccurate to bring about a problem that there is no reliability at all for the measured value. Particularly, since the tensile load is applied on the test specimen during measurement and slight lateral deviation is inevitable, this problem is fetal for the measurement.

Further, as a general problem in the existent measurement for elongation, since elongation at break is determined based on the distance between the reference lines before applying the tensile load and the final distance between the reference lines upon rupture of the test specimen by the tensile load, tensile load is applied till rupture occurs in the test specimen. However, since the test specimen scatters upon rupture depending on the material to bring about a danger, an operator has to take a safe shelter after setting the test specimen to an elongation measuring apparatus, which gives a bar to the operation efficiency.

Accordingly, it is a first object of this invention to provide a method of measuring elongation in a contactless manner not requiring setting of reference points to a test specimen, capable of obtaining an accurate measured value without using precise optical devices or conversion devices and irrespective of lateral displacement of the test specimen and further capable of being automated, as well as an apparatus for measuring elongation for practicing the method.

A second object of this invention is to provide a method of measuring the elongation described above, capable of utilizing instruments for image processing, calculative operation and control used so far in existent apparatus using television cameras as they are, as well as an apparatus for measuring the elongation for practicing the method.

A third object of this invention is to provide a method of measuring elongation capable of detecting the state just before rupture of a test specimen and determining a measured value for elongation substantially equal with that upon rupture without fracturing the test specimen, as well as an apparatus for practicing the method.

DISCLOSURE OF THE INVENTION

The first object of this invention can be attained in accordance with a first method of measuring elongation in a contactless manner while applying a tensile load to a test specimen, the method comprising irradiating laser beams from two sensor sections each integrally having a laser projector and a CCD camera to prescribed reference line positions at two positions set along the direction of elongation on the test specimen respectively, photographing the laser reflection lights by the CCD cameras respectively as speckle patterns each comprising a plurality of fringes, recognizing fringes at predetermined positions of the speckle patterns as targets corresponding to the respective prescribed reference line positions at the two positions on the coordinate of the CCD camera screens, detecting the moving amount on the pixel unit basis of the coordinate of the target fringes in the respective speckle patterns that move in accordance with the elongation of the test specimen, conducting tracking control for the two sensor sections along the direction of elongation of the test specimen by the detection signals on every movement such that the target fringes are always situated at the predetermined positions of the screens and determining elongation information for the test specimen in view of the distance between the two sensor sections, the amount of respective movement detection signals or the moving amount on the pixel unit basis of the respective target fringes.

The first method of this invention can be practiced in accordance with a first apparatus for measuring elongation of a test specimen, comprising a pair of sensor sections each having a laser projector, a CCD camera and irradiating laser beams to prescribed reference line positions at two positions along the direction of elongation of a test specimen set to a tensile strength tester, respectively, and photographing the laser reflection lights by the CCD cameras, respectively, as speckle patterns each comprising a plurality of fringes, a pair of sensor driving sections for movably supporting the pair of the sensor sections along respective guides and moving the sensor sections along the guides in accordance with input signals, respectively, a control section recognizing the fringes at predetermined positions of the speckle patterns photographed by the CCD cameras of the sensor sections as target fringes corresponding to the prescribed reference line positions, respectively, detecting the moving amount of the target fringes that move in accordance with the elongation of the test specimen on the pixel unit basis of the photographed images and controlling the pair of sensor driving sections by the detection signals such that the target fringes are situated at the predetermined positions of the speckle patterns, respectively, and an operation section for determining the elongation information for the test specimen in view of the distance between the two sensor sections, the amount of the respective movement detection signals or the moving amount on the pixel unit basis of the target fringes.

The second object of this invention can be attained also in accordance with a second method of measuring elongation in a contactless manner while applying a tensile load to a test specimen, the method comprising irradiating laser beams from two sensor sections each integrally having a laser projector and a CCD camera to prescribed reference line positions at two positions set along the direction of elongation on the test specimen, respectively, photographing the laser reflection lights by the CCD cameras respectively as speckle patterns each comprising a plurality of fringes, recognizing fringes at predetermined positions of the speckle patterns as targets corresponding to the respective prescribed reference line positions at the two positions, image converting target fringes into marks at predetermined positions of two television camera screens respectively, detecting the moving amount on the pixel unit basis of the marks of the television screens that move in accordance with the elongation of the test specimen, controlling the movement of the two sensor sections respectively along the direction of elongation of the test specimen by the detection signals on every movement such that the marks are always situated at the predetermined positions of the televisions screens, and determining the elongation information for the test specimen in view of the distance between the two sensor sections, the amount of the respective mark movement detection signals or the moving amount on the pixel unit basis of the television image marks, respectively.

The second method of this invention can be practiced in accordance with a second apparatus for measuring elongation of a test specimen, comprising a pair of sensor sections each having a laser projector and a CCD camera and irradiating laser beams to prescribed reference line positions at two positions along the direction of elongation of a test specimen set to a tensile strength tester, respectively, and photographing the laser reflection lights by the CCD cameras respectively as speckle patterns each comprising a plurality of fringes, a pair of sensor driving sections for movably supporting the pair of sensor sections along respective guides and moving the sensor sections along the guides in accordance with input signals, respectively, a pair of image conversion devices disposed corresponding to the sensor sections, respectively, and photographing the target fringes photographed by the CCD cameras of the sensor sections as marks at predetermined positions on the television camera screens, respectively, a control section recognizing the marks photographed by the television cameras 25 and 26 as reference lines corresponding to the prescribed reference line positions respectively, detecting the moving amount of the marks that move in accordance with the elongation of the test specimen on the pixel unit basis of the television screen and controlling the pair of the sensor driving sections by the detection signals such that the marks are situated at the predetermined positions of the television screens and an operation section for determining the elongation information for the test specimen in view of the distance between the two sensor sections, the amount of the respective mark movement detection signals or the moving amount on the pixel unit basis of the television image marks, respectively.

The third object of this invention can be attained by a third method embodied from each of the first or second measuring method described above, wherein stopping of images or distortion of images of speckle patterns appearing just before rupture of the application of the test specimen is sensed to stop the tensile load on the test specimen.

The third method of this invention can be practiced by a third apparatus embodied from each of the first or second apparatus described above, which further comprises a load control device that senses stopping of the images and disturbance of the images of the speckle patterns of the CCD cameras appearing just the before the rupture of the test specimen and outputting a tensile load stopping signal for the test specimen.

DESCRIPTION OF THE ACCOMPANYING DRAWINGS

DESCRIPTION OF PREFERRED EMBODIMENTS OF THE INVENTION

Preferred embodiments of this invention are to be explained with reference to the accompanying drawings.

This invention intends to measure elongation of a test specimen 2 set on a tensile strength tester 1, in which the tensile strength tester 1 is adapted to secures both ends of a test specimen 2 by chucks 3 and 4 and apply a tensile load on the test specimen 2 by pulling one or both of the chucks 3 and 4.

Figure 1:
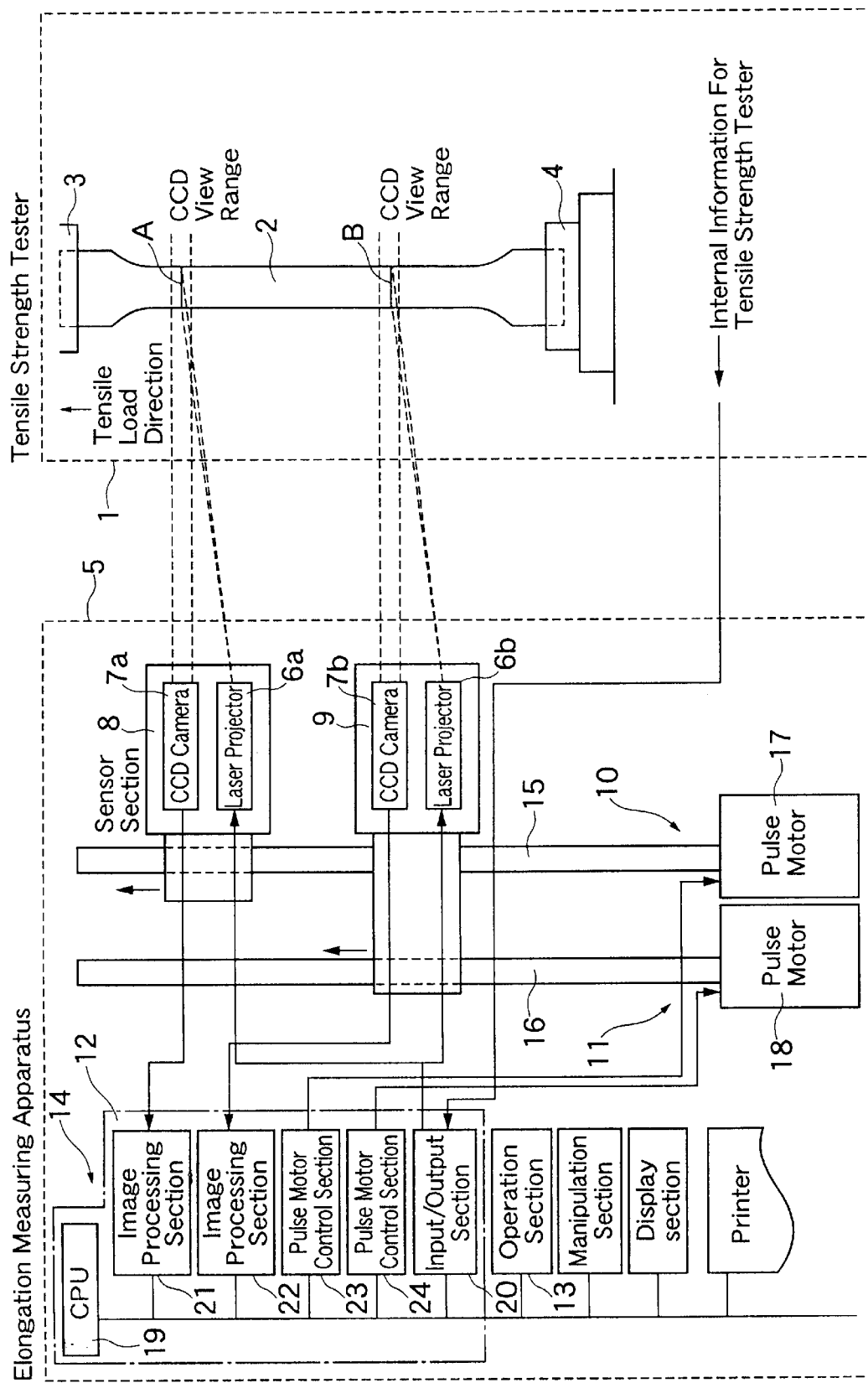
FIG. 1 is a schematic constitutional view of a first elongation measuring apparatus according to a preferred embodiment of this invention.

FIG. 1 shows the outline for a preferred embodiment of the elongation measuring apparatus used for practicing the method according to this invention. The measuring apparatus 5 includes a pair of sensor section 8 and 9 each integrally comprising a laser projector 6a or 6b and a CCD camera 7a or 7b, a pair of sensor driving sections 10 and 11 for vertically moving the sensor sections 8 and 9, respectively, in the tensile direction of the test specimen 2, a control section 12 for outputting driving signals to the sensor driving sections 10 and 11 based on the information from the sensor sections 8 and 9 and an operation section 13 for calculating elongation information such as elongation rate and elongation amount of the test specimen 2 based on various data, the controls section 12 and the operation section 13 being incorporated in a central processing unit (hereinafter referred to as a computer) 14.

The sensor sections 8 and 9 are supported on guide rods 15 and 16 of the corresponding sensor driving section 10 and 11 respectively, in which the sensor section 8 irradiates a laser beam from the laser projector 6a to one prescribed reference line position A of the test specimen and photographs the laser reflection light as a speckle pattern comprising a plurality of fringes by the CCD camera 7a. In the same manner, the sensor section 9 irradiates a laser beam from the laser projector 6b to the other prescribed reference line position B of the test specimen and photographs the laser reflection light as a speckle pattern by the CCD camera 7b.

The sensor driving sections 10 and 11 comprise a pair of driving devices, for example, the pair of guide rods 15 and 16 for supporting the sensor sections 8 and 9, respectively, and pulse motors 17 and 18 corresponding thereto, and are adapted to vertically move the sensor sections 8 and 9, respectively, along the guide rods 15 and 16 by the signals from the control section 12 to be described later. In the illustrated embodiment, the guide rods 15 and 16 are constituted as feed screw rods rotated by the pulse motors 17 and 18 so as to vertically move the sensor sections 8 and 9 by the rotation of the guide rods 15 and 16.

The control section 12 stores predetermined fringes in the speckle patterns photographed by the CCD cameras 7a and 7b in each of the sensor sections 8 and 9 as target fringes at predetermined positions on the coordinate on the basis of the pixels of the screen and when each target fringe moves on the screen, the control section 12 thereof detects the amount on the pixel unit basis, sends the detected value as a pulse signal to each of the pulse motors 17 and 18 of the sensor driving sections 10 and 11 and conducts tracking control for the sensors 8 and 9 such that each of the target fringes situates at the predetermined position in the screen.

For this purpose, the control section 12 comprises a central processing unit 19 for conducting the jobs of the measuring apparatus, an input/output section 20 for the input/output of the status information of the tensile tester 1, image processing sections 11 and 22 for A/D converting video signals of the speckle patterns inputted from the sensor sections 8 and 9 and conducting binarization of excluding intermediate tones to make the speckle patterns more distinctive, and pulse motor control sections 23 and 24 for storing the fringes each having an appropriate area from the speckle patterns as the target fringes corresponding to the respective prescribed reference line positions A and B of the test specimen 2, detecting the moving amount of each of the target fringes that moves along with elongation of the test specimen 2 as the moving amount on the coordinate corresponding to the pixels of the video screen and sending the detected signals to the pulse motors 17 and 18 of the sensor driving sections 10 and 11.

The operation section 13 is adapted to calculate the elongation rate and the elongation amount of the test specimen based on various standards between the start of the application of a tensile load and the rupture of the test specimen 2. For example, the elongation rate 67 of the test specimen 2 is determined in accordance with the following equation:

$$\delta = \frac{L - L_0}{L_0} \times 100 \ (\%)$$

where $L_0$ represents a distance between the sensor sections 8 and 9 before starting the application of the tensile load and L represents a distance between the sensor sections 8 and 9 upon rupture of the test specimen 2.

Further, the operation section 13 can calculate the elongation rate (or elongation amount) based on the moving amount of the target fringe in view of the relation between the moving amount of each of the target fringes and the moving amount of the sensor sections 8 and 9 or calculate the same based on the pulse signals in view of the relation between the pulse signals and the moving amount of the sensor sections 8 and 9.

Thus, the apparatus shown in FIG. 1 recognizes the prescribed reference line positions at two positions of the test specimen 2 as target fringes at predetermined positions in the speckle pattern, determines the movement of the prescribed reference line positions A and B that move along with elongation of the test specimen 2 as the movement of the target fringes on the coordinate in the video screen of the speckle patterns, detects the moving amount on the pixel unit basis of the video screen, conducts tracking control for the positions of the sensor sections 8 and 9 by the detection signals such that each of the target fringes situates on the predetermined position in the screen described above and measures the elongation by the relation of the moving amount or the distance between the sensor sections 8 and 9 before application of the tensile and upon rupture of the test specimen, the amount of pulse signals or the numbers of pixels along which the target fringe moves.

Figure 2:
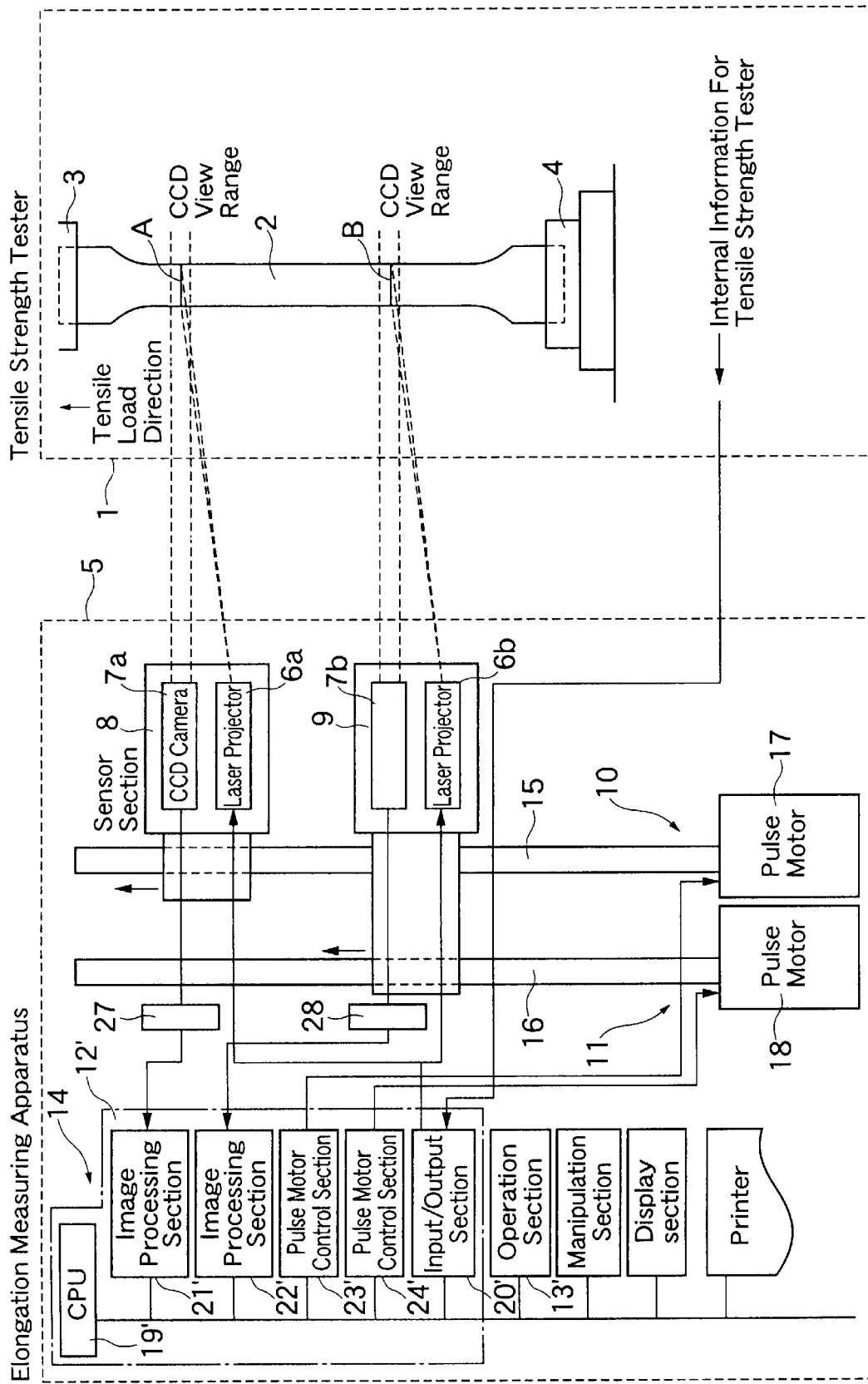
FIG. 2 is a schematic constitutional view of a second elongation measuring apparatus according to another preferred embodiment of this invention.

FIG. 2 shows a second elongation measuring method for attaining the second object of this invention, as well as a second elongation measuring apparatus used for practicing this method. Prior to the explanation for this embodiment, description is to be made for the existent measuring means adapted to photograph reference point marks attached to the test specimen by television cameras.

Figure 5:
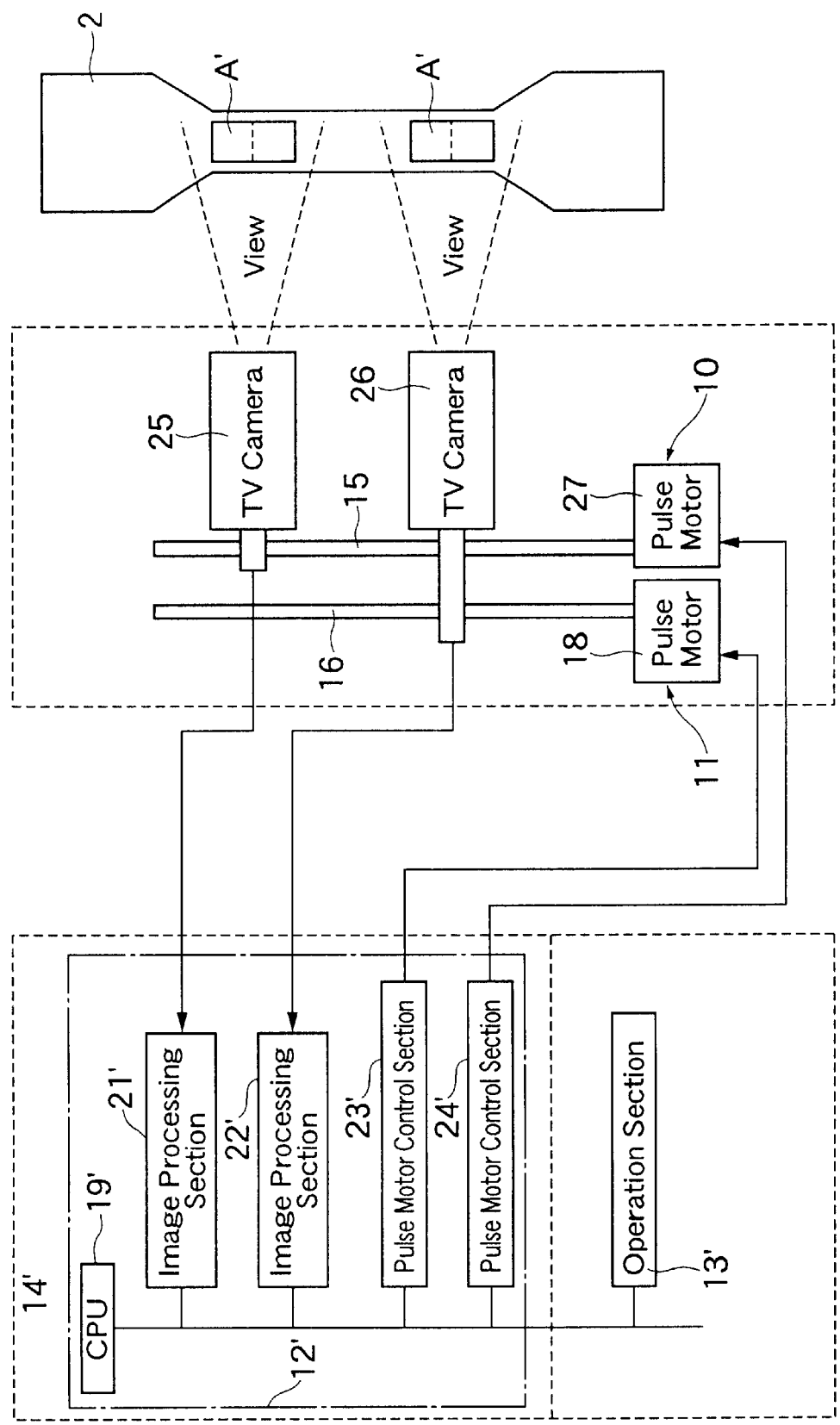
FIG. 5 is a schematic constitutional view of an existent elongation measuring apparatus for photographing reference points by television cameras.

FIG. 5 shows an example. In this apparatus, reference point marks A' and B' are appended at two specified positions of a test specimen 2, the reference point marks A' and B' at two positions are photographed respectively by two television cameras 25 and 26 individually, image processing for calculating the moving amount of the marks on the pixel unit basis is conducted by image processing sections 21' and 22' of a control section 12' to the marks in each of the camera screens during tensile test, and signals are sent based on the calculated moving amount from pulse motor control sections 23' and 24' corresponding respectively to the television cameras 25 and 26 to pulse motors 17' and 18' of camera driving sections 10' and 11' of the television cameras 25 and 26, and the television cameras 25 and 26 are controlled respectively such that each of the reference point marks A' and B' situates at the center of each of the television screens to thereby measure the elongation of the test specimen 2 based on the distance between the television cameras.

The elongation measuring means using the television cameras involves disadvantages described previously since the reference point marks A and B have to be appended to the test specimen 2.

The invention illustrated in FIG. 2 provides a second elongation measuring method and a second measuring apparatus used therefor by applying this invention explained before with reference to FIG. 1 to the measuring means on the television camera system, without appending the reference point marks A' and B', while utilizing a control section 12', image processing sections 21' and 22' and pulse motor control sections 23' and 24' and the like of a central processing unit 14 and an operation section 13' used in the existent measuring means of the television camera system as they are.

That is, the elongation measuring method converts the speckle patterns photographed by the CCD cameras 7a and 7b of the sensor sections 8 and 9 of the apparatus shown in FIG. 1 into marks at predetermined positions of the two television screens respectively, detects the moving amount of the marks in each of the television screens on the pixel unit basis that moves along with elongation of the test specimen 2, controls pulse motors 17 and 18 of the sensor driving sections 10 and 11 by the detection pulse signals, conducts tracking control for the sensor sections 8 and 9 such that the marks are always situated on the predetermined positions of the respective television screens, and measures the elongation of the test specimen 2 based on the moving amount or the distance of the two sensor sections 8 and 9, the amount of mark movement detection pulses or the moving amount of the marks on the pixel unit basis.

Figure 6:
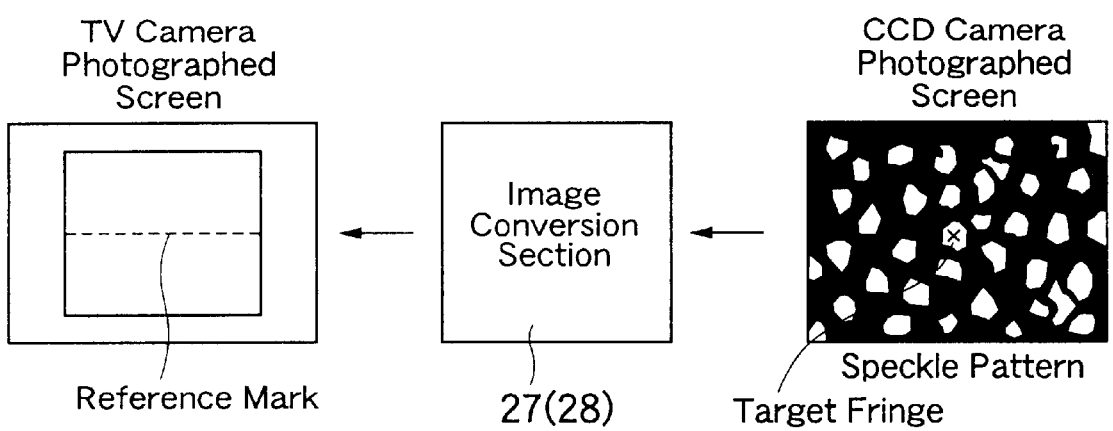
FIG. 6 is an explanatory view for the operation of an image conversion device.

For this purpose. In the apparatus shown in FIG. 2, the output of the CCD cameras 7a and 7b of the sensor sections 8 and 9 are connected by way of image conversion devices 27 and 28 with the input of the image processing sections 21' and 22' of the control section 12' that operates under the program designed for television screen, and pulse signals from the pulse motor control sections 23' and 24' designed for the television screens are inputted to the pulse motors 17 and 18 of the sensor driving sections 10 and 11 respectively. By the way, the image conversion devices 27 and 28 display the speckle patterns on the photographing screens of the CCD cameras by way of the image conversion sections to the screens of the television cameras as reference marks as shown in FIG. 6.

Thus, the apparatus shown in FIG. 2 is adapted such that the speckle pattern for each of the prescribed reference line positions photographed by the CCD cameras 7a and 7b of the sensor sections 8 and 9 is image-converted into each of the marks in the two television screens and the sensor sections 8 and 9 are position controlled in accordance with the elongation of the test specimen 2 by utilizing existent programs for television screens.

By the way, the present inventors have found that the speckle pattern of the test specimen 2 undergoing the tensile load is once stood still and then the pattern is disturbed just before the rupture of the test specimen in the course of various experiments, and have reached a novel concept that a measured value for the elongation substantially equal with the value upon rupture can be obtained without rupturing the test specimen by stopping the tensile load upon sensing the above mentioned phenomenon and measuring the elongation at the instance. That is, the elongation measuring method has a further feature of sensing stopping and disturbance of the speckle pattern just before rupture of the test specimen 2 and stopping the application of the tensile load from the tensile strength tester 1.

Figure 3:
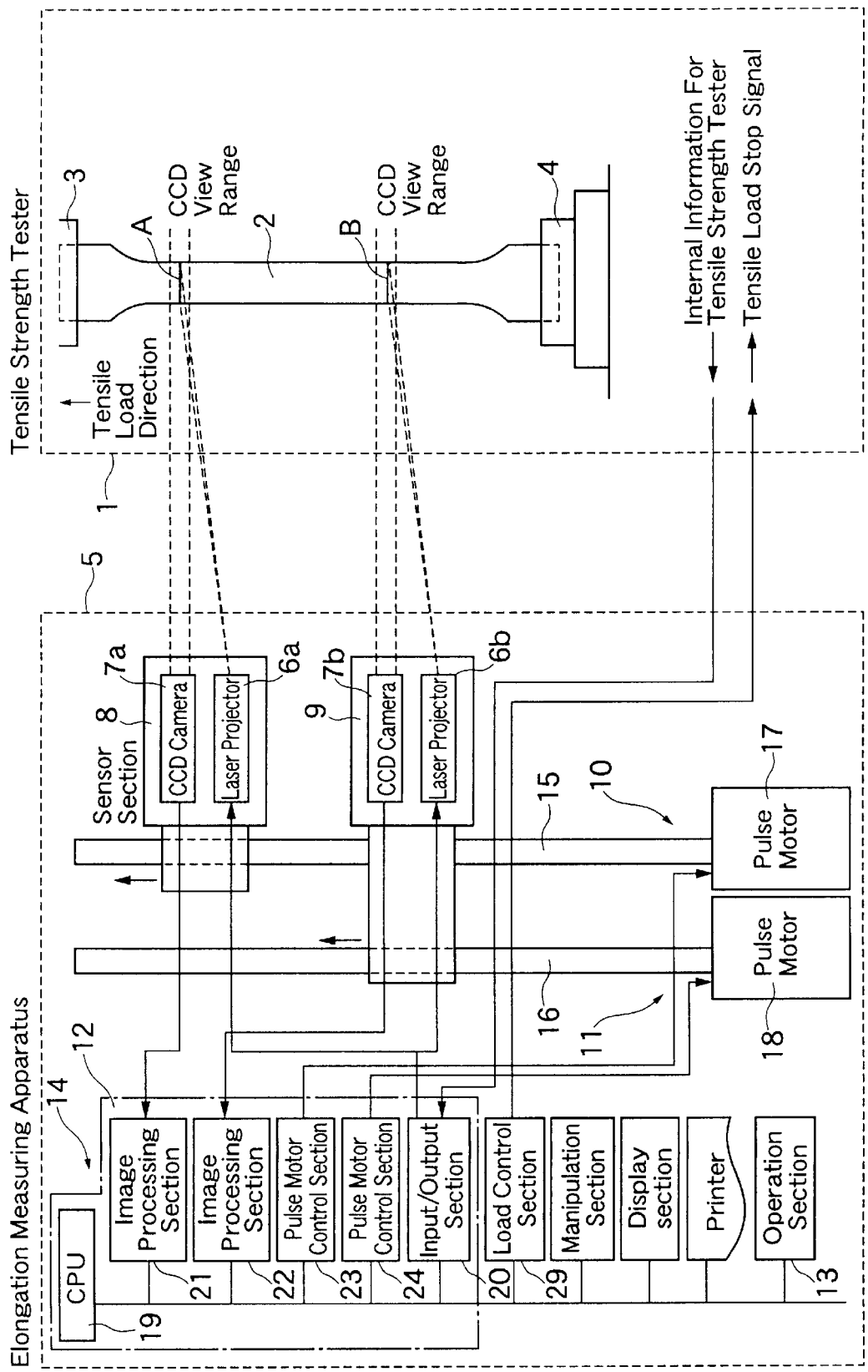
FIG. 3 is a schematic constitutional view of a third elongation measuring apparatus according to a further preferred embodiment of this invention.
Figure 4:
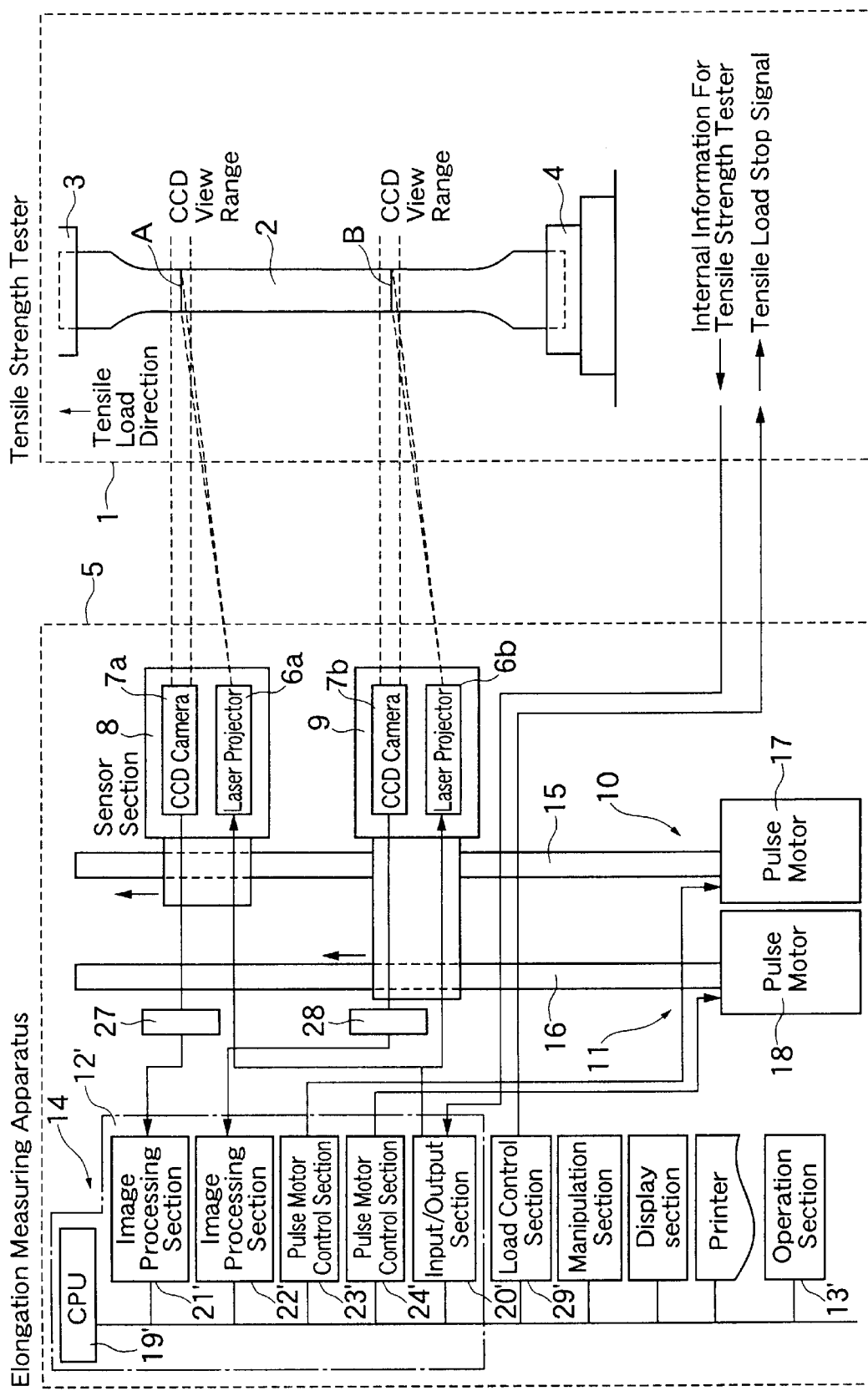
FIG. 4 is a schematic constitutional view of a modified elongation measuring apparatus according to a still further preferred embodiment of this invention.

FIG. 3 and FIG. 4 show schematic constitutions of the apparatus used in the measuring method described above, in which the apparatus shown in FIG. 3 has the same constitution as that of the apparatus shown in FIG. 1, except for the addition of a load control section 29 for sensing the stopping of the images and the distortion of the images of the speckle pattern just before rupture and stopping the application of the tensile load from the tensile strength tester 1 and the apparatus shown in FIG. 4 has the same constitution as that of the apparatus in FIG. 2 except for the addition of a load control section 29. In the illustrated embodiment, the load control section 29 is incorporated in the central processing unit 14.

What is claimed is:

1. A method of measuring elongation in a contactless manner while applying a tensile load to a test specimen 2, the method comprising irradiating laser beams from two sensor sections 8 and 9 each integrally having a laser projector 6a or 6b and a CCD camera 7a or 7b to prescribed reference line positions A and B at two positions set along the direction of elongation on the test specimen 2 respectively, photographing the laser reflection lights by the CCD cameras 7a and 7b respectively as speckle patterns each comprising a plurality of fringes, recognizing fringes at predetermined positions of the speckle patterns as targets corresponding to the respective prescribed reference line positions A and B at the two positions on the coordinate of the CCD camera screens, detecting the moving amount on the pixel unit basis of the coordinate of the target fringes in the respective speckle patterns that move in accordance with the elongation of the test specimen, conducting tracking control for the two sensor sections 8 and 9 along the direction of elongation of the test specimen 2 by the detection signals on every movement such that the target fringes are always situated at the predetermined positions of the screens and determining elongation information for the test specimen 2 in view of the distance between the two sensor sections 8 and 9, the amount of respective movement detection signals or the moving amount on the pixel unit basis of the respective target fringes.

2. A method of measuring elongation in a contactless manner while applying a tensile load to a test specimen 2, the method comprising irradiating laser beams from two sensor sections 8 and 9 each integrally having a laser projector 6a or 6b and a CCD camera 7a or 7b to prescribed reference line positions A and B at two positions set along the direction of elongation on the test specimen 2, respectively, photographing the laser reflection lights by the CCD cameras 7a and 7b respectively as speckle patterns each comprising a plurality of fringes, recognizing fringes at predetermined positions of the speckle patterns as targets corresponding to the respective prescribed reference line positions A and B at the two positions, image converting target fringes into marks at predetermined positions of two television camera screens respectively, detecting the moving amount on the pixel unit basis of the marks of the television screens that move in accordance with the elongation of the test specimen 2, controlling the movement of the two sensor sections 8 and 9 respectively along the direction of elongation oft he test specimen 2 by the detection signals on every movement such that the marks are always situated at the predetermined positions of the televisions screens, and determining the elongation information for the test specimen 2 in view the distance between the two sensor sections 8 and 9, the amount of the respective mark movement detection signals or the moving amount on the pixel unit basis of the respective television image marks.

3. A method of measuring elongation of a test specimen as defined in claim 1 or 2, wherein stopping of images or distortion of images of speckle patterns appearing just before rupture of the application of the test specimen is sensed to stop the tensile load on the test specimen.

4. An apparatus for measuring elongation of a test specimen, comprising a pair of sensor sections 8 and 9 each having a laser projector 6a or 6b, a CCD camera 7a or 7b and irradiating laser beams to prescribed reference line positions A and B at two positions along the direction of elongation of a test specimen 2 set to a tensile strength tester, respectively, and photographing the laser reflection lights by the CCD cameras 7a and 7b, respectively, as speckle patterns each comprising a plurality of fringes, a pair of sensor driving sections 10 and 11 for movably supporting the pair of the sensor sections 8 and 9 along respective guides and moving the sensor sections 8 and 9 along the guides in accordance with input signals, respectively, a control section 12 recognizing the fringes at predetermined positions of the speckle patterns photographed by the CCD cameras 7a and 7b of the sensor sections 8 and 9 as target fringes corresponding to the prescribed reference line positions A and B, respectively, detecting the moving amount of the target fringes that move in accordance with the elongation of the test specimen on the pixel unit basis of the photographed images and controlling the pair of sensor driving sections 10 and 11 by the detection signals such that the target fringes are situated at the predetermined positions of the speckle patterns, respectively, and an operation section 13 for determining the elongation information for the test specimen 2 in view of the distance between the two sensor sections 8 and 9, the amount of the respective movement detection signals or the moving amount on the pixel unit basis of the target fringes.

5. An apparatus for measuring elongation of a test specimen, comprising a pair of sensor sections 8 and 9 each having a laser projector 6a or 6b and a CCD camera 7a or 7b and irradiating laser beams to prescribed reference line positions A and B at two positions along the direction of elongation of a test specimen 2 set to a tensile strength tester, respectively, and photographing the laser reflection lights by the CCD cameras 7a and 7b respectively as speckle patterns each comprising a plurality of fringes, a pair of sensor driving sections 10 and 11 for movably supporting the pair of sensor sections 8 and 9 along respective guides and moving the sensor sections 8 and 9 along the guides in accordance with input signals, respectively, a pair of image conversion devices 27 and 28 disposed corresponding to the sensor sections 8 and 9, respectively, and photographing the target fringes photographed by the CCD cameras 7a and 7b of the sensor sections 8 and 9 as marks at predetermined positions on the television camera screens, respectively, control section 12 recognizing the marks photographed by the television cameras 25 and 26 as reference lines corresponding to the prescribed reference line positions A and B respectively, detecting the moving amount of the marks that move in accordance with the elongation of the test specimen on the pixel unit basis of the television screen and controlling the pair of the sensor driving sections 10 and 11 by the detection signals such that the marks are situated at the predetermined positions of the television screens and an operation section 13 for determining the elongation information for the test specimen 2 in view of the distance between the two sensor sections 8 and 9, the amount of the respective mark movement detection signals or the moving amount on the pixel unit basis of the television image marks, respectively.

6. An apparatus for measuring elongation of a test specimen as defined in claim 4 or 5, further comprising a load control device 29 that senses stopping of the images and disturbance of the images of the speckle patterns of the CCD cameras appearing just the before the rupture of the test specimen and outputting a tensile load stopping signal for the test specimen.

\* \* \* \* \*